Sept. 13, 196[illegible] G. C. KIRCHER Plant Pat. 2,6[illegible]
PEACH TREE
Filed Feb. 19, 1[illegible]
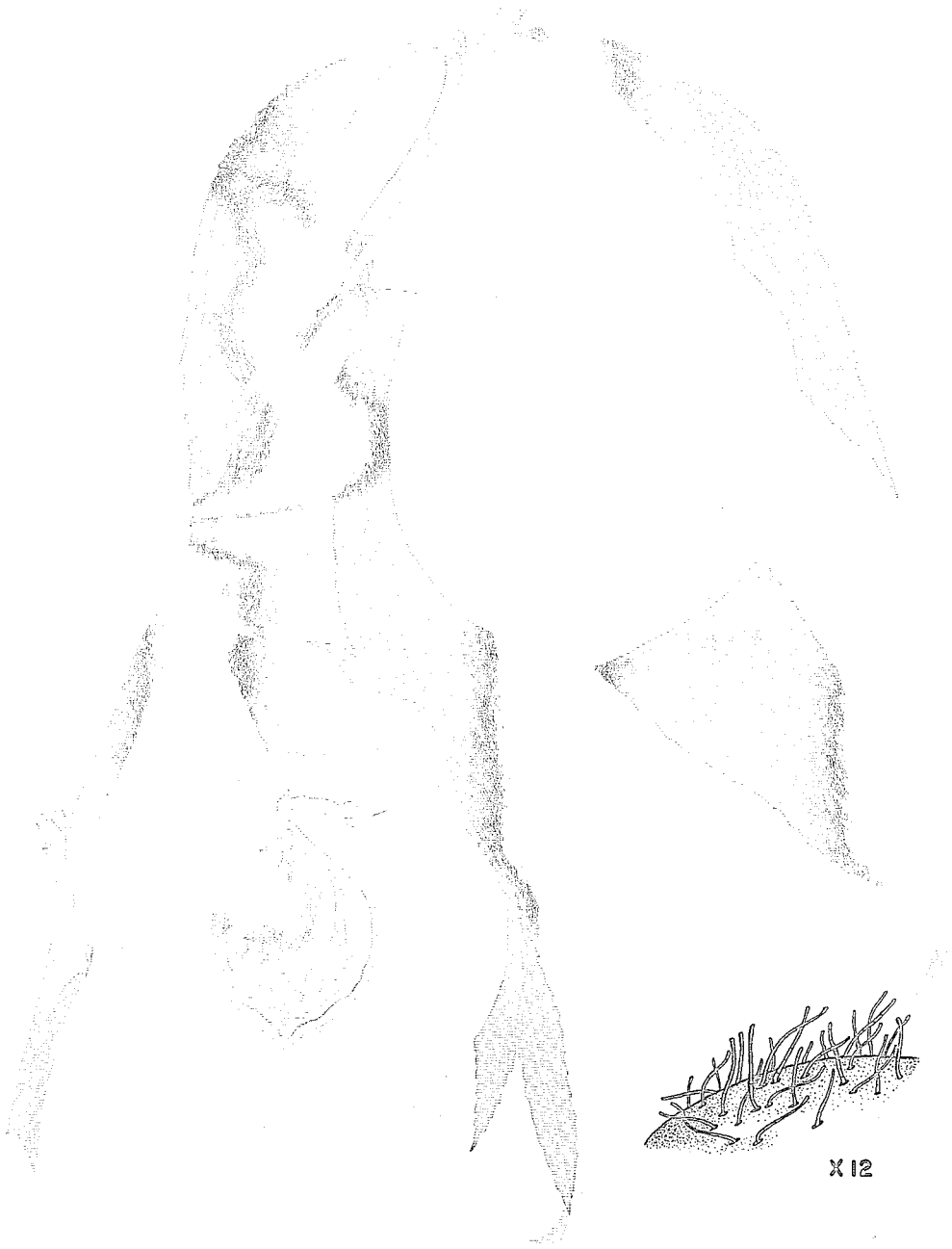
X 12
WITNESS
Samuel H. Gross
INVENTOR
George C. Kircher
by Rennwald & Gross
ATTYS.

United States Patent Office

Plant Pat. 2,671
Patented Sept. 13, 1966

2,671
PEACH TREE

George C. Kircher, 19941 Sunset Drive,
Saratoga, Calif.

Filed Feb. 19, 1965, Ser. No. 434,153
1 Claim. (Cl. Plt.—42)

This invention concerns a new and distinct variety of peach tree of the freestone, white-flesh fruit bearing kind, which resulted from breeding efforts carried on by me since 1955 in orchards at Modesto, California, with the object of developing a late, freestone variety of peach having good flavor and keeping quality large size and a firm flesh that is not mealy.

My new variety of peach tree originated as a seedling produced by crossing Hale Early (unpatented), as the seed parent, with Salwey (unpatented) as the pollen parent and its growth habit and fruit product have shown the foregoing objectives to have been accomplished, together with other desirable characteristics. The parentage was controlled by hand pollination and covering.

The tree is very sturdy and is a rapid grower producing very well in its third year. The fruit ripens in the latter part of August, at a time that does not conflict with other white peaches, most of which ripen in June, July and early August, and the fruit is of larger size and improved flavor compared to the other white peach varieties. The new variety appears to have the vigorous growing habit of the late Salwey and, like Hale Early, its fruit has a very favorable flavor and a fine juicy texture, thus avoiding the mealy texture and poor flavor of the pollen parent. The fruit is of a uniform, large size with a distinctive flavor and aroma of its own. The pubescence of the skin is coarse and does not have the wooly feel of an ordinary peach and when the fruit is ripe the skin will peel off, without a knife, leaving a white juicy peach having a delicious taste. Thus, this new variety is particularly desirable as a fresh market peach.

Asexual reproduction of my new variety by both budding and grafting, carried on by me, at Modesto, California, and at Saratoga, California, through several generations, has demonstrated that all of the aforesaid improved characteristics of the new variety are firmly fixed and hold true from generation to generation. Trees now in their fifth year show the new variety to be a regular producer of a very large crop of uniformly sized fruit. These trees are very sturdy and are rapid growers, having a top growth of three to five feet of strong wood each year, and because they are heavy producers, they must be thinned each year.

A distinctive feature of my new variety resides in the fact that the bearing wood has a tendency to run into at least two different colors. Green and red predominate and one shades into the other. This characteristic continues until the wood is two years old when there is a change to a brown coloration as the cambium layer becomes thicker. The bearing wood of most peach varieties is of reddish coloring during the first year of growth.

The growing habit of my new variety is similar to that of the variety Elberta, which is inclined to be bushy. I find, however, that my new variety can be trained easily to grow upward or can be held to a compact form, as may be desired. In either case, the new variety makes a beautiful tree and all that is required is the average cultural practice to produce abundant crops of very fine uniformly sized fruit, which is distinguished from other varieties by its appearance, size, texture, flavor, aroma, and ripening date.

The accompanying drawing shows in full color the whole fruit of my new variety of peach tree and an axial section of the fruit to illustrate its internal characteristics. The illustration also shows foliage of the new variety in color and a pen and ink sketch, showing an enlarged fragmentary view of the skin of the fruit, drawn to a scale twelve times that of the fruit and foliage, to illustrate the distinctive nature of the pubescence.

The following is a detailed description of my new variety of peach tree, the color designations being according to "A Dictionary of Color" by Maerz and Paul:

Origin: Seedling.
Parentage:
*Seed parent.*—Hale Early (unpatented).
*Pollen parent.*—Salwey (unpatented).

*The tree*

Shape: Bushy and compact.
Growth rate: Three to five feet per year.
Normal height: Held to twelve to fifteen feet by pruning.
Strength: Strong grower.
Growth habit: Vigorous and inclinded to be bushy.
Bearing wood: Color—Green 21–L–6 to 21–L–9 and Red 53–L–2 to 55–L–1 during first two years of growth, turning to a brown coloring in the third year.
Leaves:
*Size.*—Medium, 3¾ to 8½ inches long, averaging about 5 inches; 1 to 2¼ inches wide.
*Form.*—Lanceolate; acuminate tip; acuminate base; serrate margin.
*Texture.*—Glossy.
*Quantity.*—Abundant.
*Color.*—Upper side—22–L–9. Under side—21–L–6. Petiole and midrib—19–K–3 to 19–L–4.

*The flowers*

Buds:
*Size.*—Large.
*Color.*—21–B–1 for light colored parts; 15–H–1 for dark colored parts.
Blooming period: March 10th normally, and for the time of an ordinary peach blossom.
Quantity: Profuse.
Size: Medium; diameter—1 inch.
Borne: In clusters.
Shape: Cupped when first opening—form does not change, resembling the flowers of Elberta in appearance.
Color: Like that of average peach blossoms.

*The fruit*

(At picking-ripe maturity)

Maturity period: August 19 to August 25.
Size: Large.
*Axial diameter.*—3½ inches on average size of fruit.
*Diameter on suture plane.*—3 to 3¼ inches average
Form: Round, uniform.
*Suture.*—Medium, average depth.
*Ventral surface.*—Rounded.
*Apex.*—Short obtuse point.
*Cavity.*—Shape irregular; depth ½" to ⅝", breadth approximately ½".
*Markings.*—Slight blush.
Skin:
*Thickness.*—Medium.
*Color.*—Light Yellow, 9–L–4 to 9–L–6; marking—blush, 2–D–12 to 2–H–12 on side exposed to the sun.
*Pubescence.*—Firm or wiry, more widely spaced hairs than usual peach down.
Flesh:
*Texture.*—Fine and firm; juice—abundant.
*Flavor.*—Excellent; aroma—very pronounced.
*Color.*—Generally White, 9–C–1; yellowish tone around pit, 9–L–4. Surface of pit cavity—Light Red, 2–D–12 to 2–H–12. Eating quality—very good.

Stone or pit: Free. No tendency to split.

*Size.*—About 1¾ inches long; 1¼ inches wide.

*Form.*—Obovate, base-rounded; apex—sides about equal, pitted and furrowed throughout.

*Color.*—Light Red, 4–L–11 to 4–J–12.

Shipping quality: Very good.

Keeping quality: Very good.

Use: Excellent for table use; good freezing quality; very good product when dried.

The fruit of my new variety of peach tree resembles the Nectar peach in general, although Nectar is an early peach and does not size up to the new variety. Also, the flavor and appearance of the new variety are far superior to Nectar. Other white peaches presently marketed are early ripening varieties, mostly smaller in size and of inferior flavor compared to my new variety which has an attractive appearance and finds favor with all who see it and eat it.

Other advantages of my new variety of peach tree reside in its hardy, fast growing and sturdy character and the fact that it begins producing early and is a regular producer of abundant quantities of fruit during and following its third year. Its capability of being easily trained to the most desired form for appearance and harvesting and its ability to produce fruit of a large and uniform size also make the new variety a very attractive and valuable tree for decorative use as well as for commercial orchard production purposes.

Having now described my improved variety of peach tree, I claim:

A new and distinct variety of peach tree of the freestone, white-fleshed, fruit-bearing type, substantially as herein shown and described, and particularly characterized by its relatively abundant production of large fruit of substantially uniform size; its sturdy form and rapid growth of strong wood; its habit of producing fruit early in its growth; and the late August ripening period for the fruit which is distinguished by the firm juicy character of its white flesh, its unusually large size, its excellent flavor and very pronounced aroma, its freely peelable skin, its very light yellow color, and the coarse wiry nature of its pubescence.

No references cited.

ABRAHAM G. STONE, *Primary Examiner.*

ANTONIO F. GUIDA, *Examiner.*

R. E. BAGWILL, *Assistant Examiner.*